United States Patent [19]
Hayashi et al.

[11] Patent Number: 5,994,541
[45] Date of Patent: Nov. 30, 1999

[54] PROCESS FOR PRODUCING 2-AMINO-6-IODOPURINE

[75] Inventors: Taketo Hayashi; Kenji Nishiwaki; Masaaki Kuwata, all of Osaka, Japan

[73] Assignee: Sumika Fine Chemicals Co., Ltd., Osaka, Japan

[21] Appl. No.: 09/051,130

[22] PCT Filed: Jul. 28, 1997

[86] PCT No.: PCT/JP97/02617

§ 371 Date: Apr. 1, 1998

§ 102(e) Date: Apr. 1, 1998

[87] PCT Pub. No.: WO98/05663

PCT Pub. Date: Feb. 12, 1998

[30] Foreign Application Priority Data

Aug. 1, 1996 [JP] Japan ................................ 8-220328
Aug. 1, 1996 [JP] Japan ................................ 8-220329

[51] Int. Cl.[6] ................... C07D 473/40; C07B 39/00
[52] U.S. Cl. ................................................. 544/277
[58] Field of Search ............................... 544/277

[56] References Cited

U.S. PATENT DOCUMENTS 3,132,144  5/1964  Hitchings et al. .................. 260/254
5,608,064  3/1997  Singh et al. ........................ 544/277

FOREIGN PATENT DOCUMENTS 38-183981  9/1960  Japan .

OTHER PUBLICATIONS

Koda, J. Pharm. Sci. 57, 2056, 1968.
Bisacchi, J. Org. Chem 60, 2902, 1995.
R.T. Koda et al., "Synthesis of Some Iodopurine Derivatives, Journal of Pharmaceutical Sciences," pp. 2056–2061.
Abstract for JP 06–206879 (Jul. 1994).

*Primary Examiner*—Mark L. Berch
*Attorney, Agent, or Firm*—Birch, Stewart, Kolasch & Birch, LLP

[57] ABSTRACT

The process for preparing 2-amino-6-iodopurine including the steps of suspending at least one chloropurine compound selected from 2-formylamino-6-chloropurine, 2-formylamino-6-chloropurine acetate and 2-amino-6-chloropurine in a solution comprising aqueous hydriodic acid and an alkyl ketone having 3 to 7 carbon atoms; and stirring the resulting suspension at 0° to 50° C. According to the process of the present invention, 2-amino-6-iodopurine can be simply, industrially, and advantageously prepared.

4 Claims, No Drawings

PROCESS FOR PRODUCING 2-AMINO-6-IODOPURINE

This application is the national phase under 35 U.S.C. §371 of prior PCT International Application No., PCT/JP97/02617, which has an International filing date of Jul. 28, 1997, which designated the United States of America, the entire contents of which are hereby incorporated by reference.

TECHNICAL FIELD

The present invention relates to a process for preparing 2-amino-6-iodopurine. More particularly, the present invention relates to a process for preparing 2-amino-6-iodopurine, which is useful as an intermediate of antiviral agents, and the like.

BACKGROUND ART

Conventionally, 2-amino-6-iodopurine has been prepared by a method comprising reacting 2-amino-6-chloropurine with aqueous hydriodic acid at −10° C. (*J. Pharm. Sci.* 1968, 57(12), 2056–2061).

However, in this method, it is necessary to use 12 mol of expensive hydriodic acid per 1 mol of 2-amino-6-chloropurine. Also, because the yield of the resulting 2-amino-6-iodopurine is as low as about 25%, the method is not being industrially advantageous.

An object of the present invention is to provide a process for simply, industrially and advantageously preparing 2-amino-6-iodopurine.

DISCLOSURE OF INVENTION

According to the present invention, there can be provided a process for preparing 2-amino-6-iodopurine comprising the steps of suspending at least one chloropurine compound selected from 2-formylamino-6-chloropurine, 2-formylamino-6-chloropurine acetate and 2-amino-6-chloropurine in a solution comprising aqueous hydriodic acid and an alkyl ketone having 3 to 7 carbon atoms; and stirring the resulting suspension at 0° to 50° C.

BEST MODE FOR CARRYING OUT THE INVENTION

In the present invention, one of the features resides in the use of a solution comprising aqueous hydriodic acid and an alkyl ketone having 3 to 7 carbon atoms.

In the present invention, the amount of the expensive hydriodic acid can be remarkably decreased by using the above solution. Further, the desired 2-amino-6-iodopurine can be obtained at high yield of about 90%.

The chloropurine compound, a starting raw material which can be used in the present invention, is at least one member selected from 2-formylamino-6-chloropurine, 2-formylamino-6-chloropurine acetate and 2-amino-6-chloropurine as described above. The 2-formylamino-6-chloropurine, 2-formylamino-6-chloropurine acetate and 2-amino-6-chloropurine can be used alone or in admixture.

The 2-formylamino-6-chloropurine can be prepared according to conventional methods, for example, by a method disclosed in Japanese Patent Laid-Open No. Hei 6-157530.

The 2-formylamino-6-chloropurine acetate can be prepared according to conventional methods, for example, by a method disclosed in Japanese Patent Laid-Open No. Hei 6-157530.

The 2-amino-6-chloropurine is a commercially available compound. The 2-amino-6-chloropurine can be prepared according to conventional methods, for example, by a method disclosed in *J. Pharm. Sci.* 1968, 57(12), 2056–2061.

The aqueous hydriodic acid used in the present invention can be obtained by dissolving hydriodic acid in water. The concentration of hydriodic acid in the aqueous hydriodic acid is not particularly limited. It is desired that the concentration of hydriodic acid in the aqueous hydriodic acid is usually 30 to 60% by weight or so. The aqueous hydriodic acid is commercially available.

It is desired that the amount of the aqueous hydriodic acid is usually such that the amount of hydriodic acid is adjusted to 1 to 10 mol, preferably 4 to 5 mol, per 1 mol of the chloropurine compound.

Concrete examples of the alkyl ketone having 3 to 7 carbon atoms include, for example, acetone, methyl ethyl ketone, diethyl ketone, methyl isopropyl ketone, diisopropyl ketone, and the like. Among them, acetone is preferable. The alkyl ketone is a commercially available compound.

It is desired that the amount of the alkyl ketone is from 10 to 500 parts by weight, preferably from 20 to 100 parts by weight, more preferably from 40 to 70 parts by weight, still more preferably from 40 to 60 parts by weight, based on 100 parts by weight of the chloropurine compound.

2-amino-6-iodopurine is prepared by the steps of suspending the chloropurine compound in a solution comprising aqueous hydriodic acid and an alkyl ketone having 3 to 7 carbon atoms, and stirring the resulting suspension at 0° to 50° C.

During the reaction, in order to increase the reaction rate and to terminate the reaction quickly, the temperature of the suspension is 0° C. or more, preferably 25° C. or more. In addition, in order to increase the quality of 2-amino-6-iodopurine without causing hydrolysis, the temperature of the suspension is 50° C. or less, preferably 35° C. or less.

The reaction time can differ depending upon the reaction temperature, and the like. The reaction time is usually from 0.5 to 3 hours or so.

After the termination of the reaction, the resulting reaction mixture is cooled to 0° to 10° C. The reason for cooling the reaction mixture is in that there is a heat generation of about 10° C. upon adding water, so that the resulting 2-amino-6-iodopurine may be hydrolyzed when water is added to the reaction mixture having a temperature of 20° C. or more.

After cooling the reaction mixture, it is desired that water of 30 to 5° C is added to the reaction mixture. In order to sufficiently stir the reaction mixture after adding water, it is desired that the amount of water is 10 parts by weight or more, preferably 50 parts by weight or more, based on 100 parts by weight of the reaction mixture. In addition, from the aspects in consideration of the volume efficiency and economical advantages, it is desired that the amount of water is 200 parts by weight or less, preferably 100 parts by weight or less, based on 100 parts by weight of the reaction mixture.

After adding water, in order to prevent 2-amino-6-iodopurine from being hydrolyzed, an aqueous alkali solution is added to the reaction mixture while keeping the temperature of the reaction mixture 0° to 20° C., to dissolve the crystals.

Examples of the aqueous alkali solution include, for instance, aqueous sodium hydroxide, aqueous potassium hydroxide, and the like. The concentration of the aqueous alkali solution is not particularly limited. The concentration of the aqueous alkali solution may be usually 1 to 50% by weight or so. The amount of the aqueous alkali solution may usually be to an extent that the crystals dissolve.

After adding the aqueous alkali solution, activated charcoal is added to the reaction mixture. The resulting suspension is stirred for 0.5 to 2 hours at 0° to 25° C. so as not to decompose the resulting 2-amino-6-iodopurine, and the activated charcoal is then separated by filtration. An aqueous acid solution, such as an aqueous solution of hydrochloric acid, sulfuric acid, or ammonium chloride, of 10° to 60° C. is added to the resulting filtrate to neutralize the solution, and the crystals are precipitated. By collecting the precipitated crystals separated by filtration, the desired 2-amino-6-iodopurine can be obtained.

2-amino-6-iodopurine obtained by the process of the present invention is useful as an intermediate of antiviral agents.

The present invention will be more specifically described by the following examples, without intending to restrict the scope or spirit of the present invention thereto.

EXAMPLE 1

50.9 g (0.3 mol) of 2-amino-6-chloropurine was added to a mixed solution of 348.9 g (1.5 mol) of 57% by weight aqueous hydriodic acid and 31.8 ml (25.1 g) of acetone, and the formed mixture was stirred at 25° to 35° C. for one hour. 360 ml of cold water was added to the formed mixture in an ice bath, and 364.0 g (1.8 mol) of 20% by weight aqueous sodium hydroxide was then added to the mixture in the ice bath to dissolve the crystals.

9.0 g of activated charcoal was added to the solution. The resulting mixture was stirred for thirty minutes, and the activated charcoal was separated by filtration. 29.4 g (0.3 mol) of 36% hydrochloric acid was added to the resulting filtrate at room temperature.

The precipitated crystals were collected by filtration, washed twice with 200 ml of water and twice with 150 ml of methanol, and thereafter dried under reduced pressure to give 71.1 g (0.272 mol) of white crystals of 2-amino-6-iodopurine. The yield was 90.8%.

The IR spectrum of the resulting crystals was identical to that of the crystals prepared by the method described in *J. Pharm. Sci.* 1968, 57(12), 2056–2061.

EXAMPLE 2

12.9 g (0.050 mol) of 2-formylamino-6-chloropurine acetate was added to a mixed solution of 56.1 g (0.250 mol) of 57% by weight aqueous hydriodic acid and 10 ml (7.9 g) of acetone, and the formed mixture was stirred at 25° to 35° C. for one hour. 25 ml of cold water was added to the formed mixture in an ice bath, and 83.0 g (0.420 mol) of 20% by weight aqueous sodium hydroxide was then added to the mixture to dissolve the crystals.

2.7 g of activated charcoal was added to the solution. The resulting mixture was stirred for 15 hours, and the activated charcoal was separated by filtration. 40.0 g (0.150 mol) of 20% aqueous ammonium chloride kept at 50° C. was added to the resulting filtrate.

The precipitated crystals were collected by filtration, washed twice with 20 ml of water and twice with 20 ml of methanol, and thereafter dried under reduced pressure to give 11.6 g (0.044 mol) of crystals of 2-amino-6-iodopurine. The yield was 88.9%.

The IR spectrum of the resulting crystals was identical to that of the crystals prepared by the method described in *J. Pharm. Sci.* 1968, 57(12), 2056–2061.

EXAMPLE 3

9.9 g (0.050 mol) of 2-formylamino-6-chloropurine was added to a mixed solution of 56.1 g (0.250 mol) of 57% by weight aqueous hydriodic acid and 10 ml (7.9 g) of acetone, and the formed mixture was stirred at 25° to 35° C. for one hour. 25 ml of cold water was added to the formed mixture in an ice bath, and 60.0 g (0.300 mol) of 20% by weight aqueous sodium hydroxide was then added to the mixture to dissolve the crystals.

2.7 g of activated charcoal was added to the solution. The resulting mixture was stirred for 15 hours, and the activated charcoal was separated by filtration. 40.0 g (0.150 mol) of 20% aqueous ammonium chloride kept at 50° C. was added to the resulting filtrate.

The precipitated crystals were collected by filtration, washed twice with 20 ml of water and twice with 20 ml of methanol, and thereafter dried under reduced pressure to give 11.7 g (0.045 mol) of crystals of 2-amino-6-iodopurine. The yield was 90.0%.

The IR spectrum of the resulting crystals was identical to that of the crystals prepared by the method described in *J. Pharm. Sci.* 1968, 57(12), 2056–2061.

It is clear from the results of Examples 1 to 3 that 2-amino-6-iodopurine can be simply prepared by Examples 1 to 3.

INDUSTRIAL APPLICABILITY

According to the process of the present invention, 2-amino-6-iodopurine, which is useful as an intermediate of antiviral agents, can be simply, industrially, and advantageously obtained.

We claim:

1. A process for preparing 2-amino-6-iodopurine comprising the steps of:

suspending at least one chloropurine compound selected from 2-formylamino-6-chloropurine, 2-formylamino-6-chloropurine acetate and 2-amino-6-chloropurine in a solution comprising aqueous hydriodic acid and a ketone of 3 to 7 carbon atoms having at least one alkyl group; and stirring the resulting suspension at 0° to 50° C.

2. The process for preparing 2-amino-6-iodopurine according to claim 1, wherein an amount of said aqueous hydriodic acid is 1 to 10 mol, per 1 mol of said chloropurine compound.

3. The process according to claim 1, wherein an amount of said ketone is from 10 to 500 parts by weight, based on 100 parts by weight of said chloropurine compound.

4. The process according to claim 1, wherein said ketone is acetone, methyl ethyl ketone, diethyl ketone, methyl isopropyl ketone or diisopropyl ketone.

* * * * *